United States Patent [19]

Baer

[11] Patent Number: 5,600,858
[45] Date of Patent: Feb. 11, 1997

[54] PATIENT SUPPORT FOR USE IN A MEDICAL APPARATUS

[75] Inventor: Ulrich Baer, Neunkirchen, Germany

[73] Assignee: Siemens Aktiengesellschaft, Munich, Germany

[21] Appl. No.: 428,416

[22] Filed: Apr. 25, 1995

[30] Foreign Application Priority Data

May 6, 1994 [DE] Germany .................. 44 16 202.2

[51] Int. Cl.⁶ .................................................. A61G 13/00
[52] U.S. Cl. ................ 5/601; 5/181; 5/943; 378/209
[58] Field of Search .................... 5/601, 943, 181; 378/208, 209

[56] References Cited

U.S. PATENT DOCUMENTS 4,034,224  7/1977  Heavens et al. .................. 5/601
4,910,819  3/1990  Brown .............................. 378/209
4,984,774  1/1991  Zupanic et al. .................. 5/601

FOREIGN PATENT DOCUMENTS 4224036  5/1993  Germany .
4330606  7/1994  Germany .

*Primary Examiner*—Michael F. Trettel
*Attorney, Agent, or Firm*—Hill, Steadman & Simpson

[57] ABSTRACT

A patient support mechanism for use in a medical examination or therapy apparatus for supporting a patient has a frame on which a patient support plate is carried, the frame having substantially horizontally aligned surfaces laterally disposed at longitudinal sides of the support plate. The support plate has regions along its longitudinal sides which extend over and at least partially cover the horizontally aligned surfaces of the frame.

5 Claims, 1 Drawing Sheet

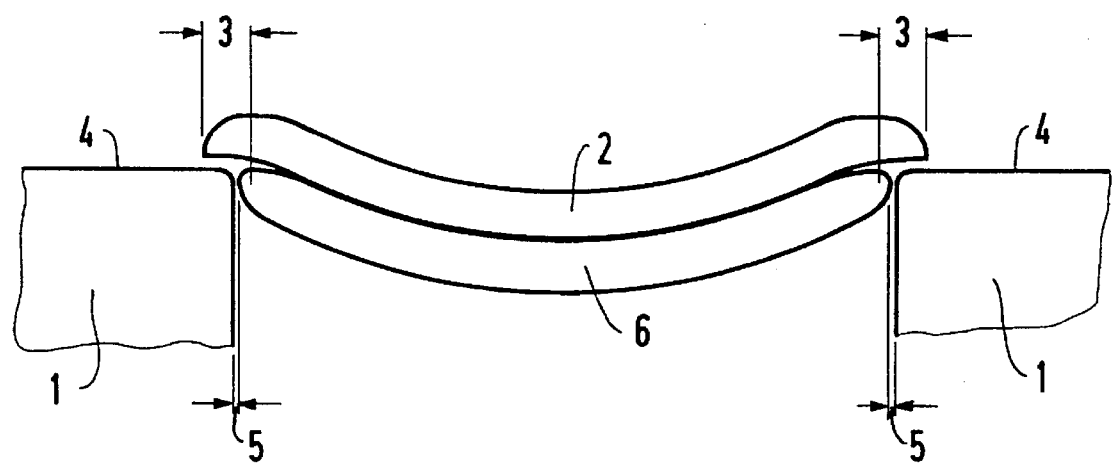

PATIENT SUPPORT FOR USE IN A MEDICAL APPARATUS

BACKGROUND OF THE INVENTION

1. Field of the Invention

The present invention is directed to a patient support for use in a medical apparatus of the type having a frame on which a patient support plate is carried.

2. Description of the Prior Art

In order to support a patient in a medical apparatus, such as radiographic installations, computer tomography apparatuses, a patient support mechanism is provided having a supporting surface or table for the patient which is mounted on a frame. The frame typically has two spaced surfaces, which are approximately horizontally aligned, with the support surface for the patient being disposed between these two frame surfaces. The support mechanism permits the patient to be supported and positioned with respect to an exposure unit.

The support surface for the patient may have a rigid connection to the frame, or may be mounted to the frame so as to be movable, at least in the longitudinal direction of the support surface. In all cases, the support plate is disposed completely between the frame surfaces, with a gap being present between each side of the support plate and the adjacent frame surface. This is particularly so in the case of longitudinally adjustable support plates. The presence of these gaps on either side of the support plate constitutes a hazard, because articles can fall into this gap or cables and other electrical lines can become clamped therein, so that the operating dependability of the patient support mechanism is disturbed.

SUMMARY OF THE INVENTION

It is an object of the present invention to provide a patient support mechanism of the type having a supporting surface for the patient disposed between two substantially aligned surfaces of a frame, which is not subject to disruptions in the operating dependability of the mechanism.

The above object is achieved in accordance with the principles of the present invention in a patient support having a patient supporting surface disposed between two substantially horizontally aligned surfaces of a frame, with the supporting surface having two long, or longitudinally extending, sides with each of these long sides at least partially extending over and covering each of the horizontally aligned surfaces of the frame.

In the supporting mechanism of the invention, a gap may still exist between the frame and a part of the overall support plate, however, this gap, which extends vertically relative to the support plate, will be covered by the aforementioned portions of the support plate which extend over the frame, and therefore the gap no longer presents a hazard.

DESCRIPTION OF THE DRAWING

The single figure is an end elevational view of a patient support assembly constructed in accordance with the principles of the present invention.

DESCRIPTION OF THE PREFERRED EMBODIMENTS

A portion of a patient support assembly constructed in accordance with the principles of the present invention is shown in an end view in the drawing. The patient support assembly includes a frame 1 which carries a patient support plate 2, the frame being supported on the floor of an examination room. The support plate 2 may be connected to the frame by means of a rigid connection, but can alternatively be mounted at the frame 1 so as to be adjustable at least along the longitudinal axis of the support plate 2 (i.e., in and out of the plane of the drawing). The frame 1 may also carry the support plate 2 in a manner so that the support plate 2 is height-adjustable or pivotable.

The frame 2 has surfaces 4 which are substantially horizontally aligned, with the support plate 2 extending between these surfaces 4. The support plate 2, in accordance with the principles of the present invention, has regions 3 along the longer (longitudinally extending) sides of the support plate 2 which partially cover the surfaces 4 of the frame 1. Articles are thus prevented from falling into a gap which exists between the frame 1 and a portion of the support plate 2 which extends between the frame surfaces 4. The portion of the support plate 2 which extends between the surfaces 4 may, for example, be a carrier plate 6, however, this is not important to the inventive concept disclosed herein, and if the support plate 2 is sufficiently rigid, the carrier plate 6 can be dispensed with. If a carrier plate 6 is used, however, the support plate 2 may be in the form of a compressible mat of polyurethane or polyethylene. Other suitable material may be employed, particularly materials having an x-ray absorption which substantially corresponds to a water equivalent.

The support plate 2 is preferably fashioned with a curve between the surfaces 4, so as to support a patient thereon in a stable manner. It should be assured that the support plate 2 has sufficient stability so that the regions 3 do not rest on the surfaces 4, even when the support plate 2 is loaded with a patient, in order to avoid friction when the support plate 2 is longitudinally displaced relative to the frame 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. A patient support apparatus comprising:

a frame having two substantially horizontally aligned surfaces spaced from each other;

a patient support plate carried by said frame, said patient support plate having longitudinal sides adjoining said frame;

said patient support plate having regions of said longitudinal sides extending in self-supporting, undraped fashion over and at least partially covering said horizontally aligned surfaces of said frame; and said patient support plate being downwardly curved between said surfaces of said frame.

2. A patient support apparatus as claimed in claim 1 further comprising a carrier plate disposed beneath said patient support plate, said carrier plate being contained exclusively between said horizontally aligned surfaces and not covering said horizontally aligned surfaces.

3. A patient support apparatus as claimed in claim 2 wherein said carrier plate is rigid, and wherein said patient support plate comprises a compressible mat.

4. A patient support apparatus as claimed in claim 3 wherein said compressible mat comprises material selected from the group consisting of polyurethane and polyethylene.

5. A patient support apparatus as claimed in claim 1 wherein said support plate is carried by said frame for adjustment of said support plate relative to said frame along a longitudinal axis of said support plate.

* * * * *